United States Patent
Annavi et al.

(10) Patent No.: US 10,991,460 B2
(45) Date of Patent: Apr. 27, 2021

(54) METHOD AND SYSTEM FOR IDENTIFICATION OF CEREBROVASCULAR ABNORMALITIES

(71) Applicant: NEUROANALYTICS PTY LTD., Kew (AU)

(72) Inventors: Prabhakar Annavi, Bangalore (IN); Nandakishor, West Melbourne (AU)

(73) Assignee: NEUROANALYTICS PTY LTD., Kew (AU)

( * ) Notice: Subject to any disclaimer, the term of this patent is extended or adjusted under 35 U.S.C. 154(b) by 3 days.

(21) Appl. No.: 16/365,548

(22) Filed: Mar. 26, 2019

(65) Prior Publication Data
US 2020/0020435 A1    Jan. 16, 2020

(30) Foreign Application Priority Data
Jul. 13, 2018 (IN) .............................. 201841026289

(51) Int. Cl.
| | | |
|---|---|---|
| *G16H 30/40* | (2018.01) | |
| *G16H 50/50* | (2018.01) | |
| *G06K 9/00* | (2006.01) | |
| *G06T 7/00* | (2017.01) | |
| *G06N 3/08* | (2006.01) | |
| *G16H 50/30* | (2018.01) | |
| *A61B 5/00* | (2006.01) | |

(52) U.S. Cl.
CPC .......... *G16H 30/40* (2018.01); *G06K 9/0014* (2013.01); *G06N 3/08* (2013.01); *G06T 7/0012* (2013.01); *G16H 50/50* (2018.01); *A61B 5/0042* (2013.01); *A61B 5/4064* (2013.01); *A61B 2576/026* (2013.01); *G06K 9/00147* (2013.01); *G16H 50/30* (2018.01)

(58) Field of Classification Search
CPC ........ G16H 30/40; G16H 50/50; G16H 50/30; G06K 9/0014; G06K 9/00147; G06N 3/08; G06T 7/0012; A61B 5/0042; A61B 5/4064; A61B 2576/026
See application file for complete search history.

(56) References Cited

U.S. PATENT DOCUMENTS

| | | | |
|---|---|---|---|
| 9,349,176 B2 | 5/2016 | Yang et al. | |
| 2014/0316758 A1* | 10/2014 | Yagi ....................... | A61B 90/37 703/9 |
| 2018/0121760 A1* | 5/2018 | Santannaria-Pang ........................ | G06K 9/6274 |

* cited by examiner

*Primary Examiner* — David F Dunphy
(74) *Attorney, Agent, or Firm* — Maschoff Brennan

(57) ABSTRACT

System and methods are disclosed for identifying as well as distinguishing between cerebrovascular abnormalities. The system comprises a medical imaging device configured for capturing plurality of images of a cerebrovascular region of a subject and communicating the same to a computing device. The computing device comprises one or more modules configured for extracting features from the captured images, grouping the cerebrovascular region into one of blood vessel type and non-blood vessel type and further extracting features associated with the blood vessels to classify each point on the blood vessel into one of a non-branching, converging and diverging type. The system further comprises a user interface for interactively viewing the results of the classification thereby providing a means to identify cerebrovascular abnormalities.

10 Claims, 3 Drawing Sheets

3A

3B

3C

METHOD AND SYSTEM FOR IDENTIFICATION OF CEREBROVASCULAR ABNORMALITIES

TECHNICAL FIELD

The present disclosure relates to vascular disease detection and more particularly relates to a method and system for cerebrovascular disease detection using image processing and convolutional neural networks.

BACKGROUND

Generally, cerebrovascular disease includes a variety of medical conditions that affect the blood vessels of the brain and blood flow through the network of cerebral arteries and veins supplying to the brain. The arteries deliver oxygenated blood and other nutrients to the brain, and the veins carry deoxygenated blood back to the heart, removing carbon dioxide, lactic acid, and other metabolic products. Any change in the structure of the arteries or the veins results in cerebrovascular diseases which may be broadly classified into non-aneurysm and aneurysm related diseases.

Early diagnosis and treatment of cerebrovascular diseases is very important in preventing morbidity or death. With the advancement in technology, computed tomography (CT) perfusion imaging, digital subtraction angiography, CT angiography, etc. are frequently applied as an alternative to invasive angiograph, to evaluate hemodynamic changes and to visualize lesions in patients with acute cerebrovascular diseases. For example, a conventional system for cerebrovascular disease detection comprises a computed tomography (CT) scanner which enables the acquisition of high quality CT angiography (CTA) images and one or more processors that assigns points of interest (POIs) in the image data/images. That is, the one or more processors assign POIs on blood vessels within an image of a subject based on defined characteristics that are associated with a cerebrovascular condition, calculates one or more features of each POI, and identifies one or more cerebrovascular abnormality suspects based on the calculated features, wherein calculating the one or more features comprises one of calculating a distance from the POI to a centre line, calculating a radius of the vessel, calculating a planeness of the vessel at the POI, calculating a shape index at the POI, etc.

Further, various algorithms are developed for automated detection of cerebrovascular diseases using CTA images. However such algorithms rely on the local image features extracted along vascular branches, and hence are only able to produce local predictions that independently characterize centreline points along the vascular branch. Further, conventional algorithms generally fall short of the accuracy levels needed to achieve real clinical utility, due to the high variability in shape and appearance of abnormalities. For example, the conventional systems fail to detect rare abnormalities such as cerebral venous malformations—as these include abnormal connection between arterial and venous system bridged by abnormal channels which are tortuous and non-spherical in nature. Further, the conventional systems fail to detect developmental venous anomaly—a bundle of abnormally developed veins, dissecting aneurysm, thrombosed aneurysm, etc.

SUMMARY OF THE DISCLOSURE

Thus there exists a need for a system and method which mitigates at least some of the disadvantages of the state of the art.

This summary is provided to introduce a selection of concepts in a simple manner that are further described in the detailed description of the disclosure. This summary is not intended to identify key or essential inventive concepts of the subject matter nor is it intended for determining the scope of the disclosure.

A method and system for identifying cerebrovascular abnormalities using image processing and convolutional neural networks is disclosed. In some embodiments of the present disclosure, the method comprises the steps of constructing a virtual representation of a circulatory system from cerebral region of a subject, wherein the virtual representation is constructed using a plurality of images of the cerebral region captured by a medical imaging device; classifying each spatial position in the virtual representation into a blood vessel type and non-blood vessel type using convolutional neural network features (CNN features); generating a graphical representation of the blood vessel network using the output of the classification; further classifying each position in the graphical representation of the blood vessel network into a converging type, a diverging type and a non-branching type using the plurality of CNN features and derived features; displaying the annotated graphical representation of the blood vessel network on a user interface; receiving user selection of regions of interest within the graphical representation; processing the selected region of interest using one of a graph convolutional network architecture or a GNU-LSTM architecture to identify one or more cerebrovascular abnormalities.

In some embodiments, the system of the present disclosure comprises a medical imaging device configured for capturing a plurality of images of cerebral region of a subject and communicating the plurality of images to a computing device; the computing device comprises a receiving module configured for receiving the plurality of images and further for storing the images in a storage unit of the computing device; the computing device further comprises a graphical processing module configured for reconstructing a two dimensional or three dimensional virtual representation of the circulatory system in cerebral region of the subject; an extractor module configured for implementing a convolutional neural network for extracting a plurality of features associated with the input image; a classifier module configured for classifying each spatial position in a graphical representation of the blood vessel network into a converging type, a diverging type and a non-branching type; and a user interface configured for displaying the graphical representation of the blood vessel network and for receiving a user selection of the regions of interest within the graphical representation for further diagnosis; the classifier module coupled with the processor are configured for receiving the input from the user interface and processing the input graphical representation for identifying one or more cerebrovascular abnormalities.

BRIEF DESCRIPTION OF THE FIGURES

The disclosure will be described and explained with additional specificity and detail with the accompanying figures in which.

Figure 1:
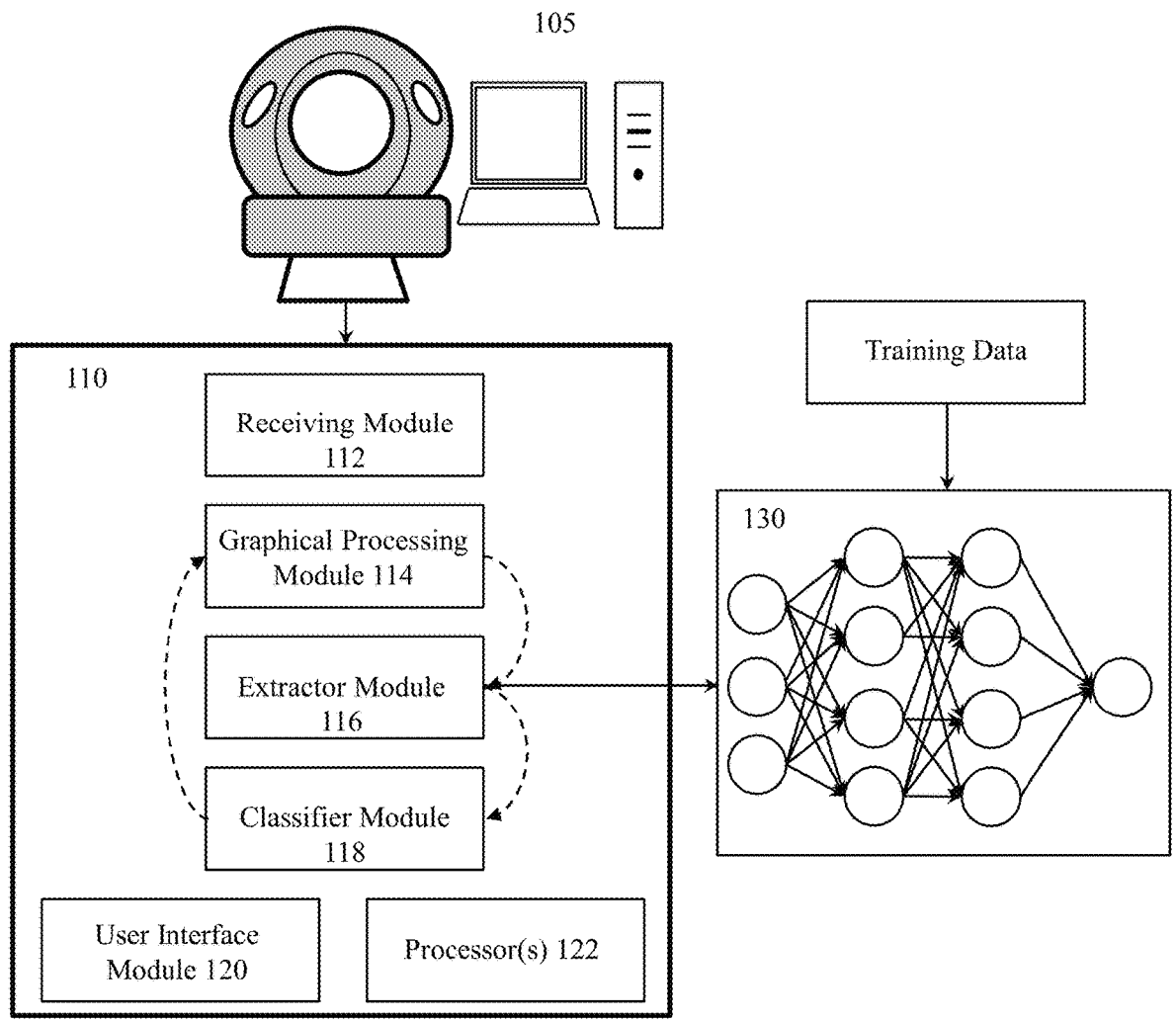
FIG. 1 illustrates a system for identifying cerebrovascular abnormalities in a subject, in accordance with various embodiments of the present disclosure.

Further, persons skilled in the art to which this disclosure belongs will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those of ordinary skill in the art having benefit of the description herein.

DETAILED DESCRIPTION OF THE EXEMPLARY EMBODIMENTS

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The system, methods, and examples provided herein are illustrative only and not intended to be limiting.

Embodiments of the present disclosure will be described below in detail with reference to the accompanying figures.

The embodiments herein disclose a method and system for identifying cerebrovascular abnormalities in a cerebral region of a subject using a virtual representation of the circulatory system in the cerebral region coupled with features extracted using a convolutional neural network.

Now referring to FIG. 1, a system for identifying cerebrovascular abnormalities in a subject is disclosed. The system comprises a medical imaging device 105 that is configured for capturing plurality of images of cerebral region of the subject. The medical imaging device 105, is optionally in communication with a computer for selecting the regions of interest, for running software to optimize the device 105, calibration and such. The medical imaging device 105 is for example a 64 slice or a 256 slice CT angiography device. Typically, an intravenous radiocontrast material is administered to the subject before scanning the areas of interest using the CT angiography device. The medical imaging device 105 is operatively connected to a computing device 110 via a communication network. The communication network is, for example, a wired or wireless network. Optionally, the medical imaging device 105 is also connected to a remote server via the communication network for archiving the medical image data captured by the device 105 over a period of time.

The computing device 110 is configured for operating a plurality of modules, each executing one or more processes leading to analysis of the medical image data received from the medical imaging device 105 for identifying one or more cerebrovascular abnormalities. The computing device 110 comprises a receiver module 112, a graphical processing module 114, an extractor module 116, a classifier module 118, a user interface 120 and a processor 122 coupled to a storage unit, for example. The processor 122 is preferably a graphical processing unit (GPU) capable of processing image data efficiently.

The receiver module 112 receives the medical image data comprising a plurality of images pertaining to the cerebral region of a subject, from the medical imaging device 105. In an embodiment, the receiver module 112 may comprise a filtering mechanism for sorting or selecting most suitable images of the cerebral region for further analysis. Further, the receiver module 112 stores the images and other medical data in the storage unit of the computing device 110.

The graphical processing module 114 is configured for reconstructing a two dimensional or three dimensional map of the circulatory system from the images received by the computing device 110. The images pertaining to the region of interest, i.e. the cerebral region of the subject are processed by the graphical processing module 114 using methods such as surface rendering technique, non-stereo corresponding contour method etc. known in the art, to reconstruct the circulatory system depicting blood vessels and other tissues in the cerebral region. The two dimensional or three dimensional reconstruction of the circulatory system of the cerebral region is referred to as 'virtual representation' of the cerebral region.

The extractor module 116 is configured to perform the inventive feature extraction process in accordance with embodiments of the present disclosure. With the two dimensional or three dimensional virtual representation of the cerebral region as the input, the extractor module 116 executes a convolutional neural network (CNN) or deep convolutional neural network to extract the CNN features associated with the virtual representation. In one example, the convolutional neural network is implemented at the computing device 110 itself. In another example, the extractor module 116 communicates with a network of computers implementing the convolutional neural network via the communication network, wherein each computing unit acts as a 'node'. The plurality of computing nodes constitute an input layer, a hidden layer and an output layer of the convolutional neural network, each of the plurality of computing nodes extract features from the input and may additionally learn the features to be extracted from a training data set. In one example, the training data set may be generated using generative adversarial network (GAN). In another example, the plurality of images captured by the medical imaging device 105 and archived at the remote server may be used as a training data set. The plurality of CNN features extracted by the extractor module 116 may further be processed by the processor 122 of the computing device 110 to derive one or more additional features, referred to as 'derived features'.

Typically, each node in the one or more layers of the convolutional neural network comprise learnable filters that detect specific types of features associated with each of the one or more spatial positions in the input. As a result, for the input provided by the graphical processing module 114, comprising the virtual representation of cerebral region of the subject, the extractor module 116 coupled with the convolutional neural network extract plurality of features associated with the virtual representation. These features are now referred to as 'CNN features'. The extracted CNN features are further stored in a database (not shown) of the computing device 110.

In one implementation, in order to obtain a precise image with fewer training images, the convolutional neural network (CNN) of the extractor module 116 is arranged to have several layers for extracting plurality of features followed by a concatenation or pooling operation to improve the precision of output image. In contrast to the conventional CNN models, in this approach, the successive layers of the network are used for filtering the features and upsampling the image data instead of carrying our pooling operation. This results in increasing the resolution of the output.

In another implementation, the extractor module 116 implements a variant of CNN called capsule neural network wherein the pooling operation is replaced by the layers in a child and parent topology such that each child layer predicts the output from a parent layer such that over a period of time, the learnings converge to give a high resolution output.

The classifier module 118 is configured to perform one or more classification processes on the medical image data. In one embodiment, the classifier module 118 executes functions and processes to classify the regions in virtual representation into blood vessel type and non-blood vessel type using the CNN features extracted by the extractor module 116. For meeting the objective of the present disclosure, it is desirous to have a highly accurate representation of the actual circulation system for better diagnosis. The classifier module 118 results in generating such an accurate representation of the circulatory system by classifying the regions in virtual representation of the cerebral region into blood vessel type and non-blood vessel type such as tissues, collagen etc. The classifier module identifies each spatial position in the virtual representation into one of the two categories—blood vessel type and non-blood vessel type using the CNN feature vectors provided as an input to the classifier module 118.

Further, the graphical processing module 114 is configured for generating a graphical representation of each of the one or more blood vessels as identified by the classifier module 118 using the output of classifier module 118 and extractor module 116. Specifically, the graphical processing module 114 creates a graphical representation of each blood vessel in the cerebral region wherein each spatial position in the graphical representation is generated using features extracted by the extractor module 116 including but not limited to the CNN features. The CNN features and derived features include, for example, centre of blood vessel, radius of blood vessel, texture, blood flow direction, volume of the area under consideration, relative position of the area under consideration with respect to centre of the cerebral region etc. In addition, the graphical representation of the blood vessels in the cerebral region generated by the graphical processing module 114 may be a two dimensional representation—in which case, dimensions at the edges of blood vessel are directly proportional to thickness of the blood vessel or a three dimensional representation—in which case, dimensions at the edges of blood vessel are directly proportional to volume of blood flow through the blood vessel. It is to be noted that the characteristics of the blood vessel such as thickness and volume of blood flow are derived from the features extracted by the extractor module 116.

The classifier module 118 is further configured for classifying the blood vessels in the graphical representation generated by the graphical processing module 114 into one of a diverging type, converging type and non-branching type. In one example, the classifier module 118 implements a graph convolutional network (GCN) to classify each spatial position on each of the one or more blood vessels in the graphical representation into one of a diverging type, converging type and non-branching type. The graphical representation is further annotated with this classification data using colour codes, alphanumeric legends etc.

The user interface 120 is configured for displaying the graphical representation of the blood vessels in the cerebral region on a graphical display interface, for example. In one embodiment, the user interface 120 is interactive and capable of receiving instructions from users of the computing device 110. The users are for example, doctors and healthcare professionals. In one example, the user interface 120 displays the graphical representation in an ellipsoid depicting the cross-sectional view of brain of the subject. Further the user interface 120 is configured to receive a selection of area of interest within the graphical representation, wherein the area of interest is selected from the centre of the ellipsoid to the circumference in preferably one direction. The selection of area of interest is received via touch screen of the user interface 120, for example. In one example, multiple areas of interest are selectable by the user.

The area of interest selected by the user is further processed to identify one or more cerebrovascular abnormalities within the cerebral region of the subject. In one embodiment, the network of blood vessels within the graphical representation of the selected area of interest is provided as input to the classifier module 118. The classifier module 118 executes a second graph convolutional network to classify the selected area of interest using the attributes of rare cerebrovascular abnormalities such as developmental venous anomaly (DVA) and the features of the spatial positions in the network of blood vessels within the graphical representation.

In another embodiment, the classifier module 118 implements a GNU-LSTM (long short term memory) architecture that receives the plurality of features and the classification for each spatial position in the network of blood vessels (i.e. converging type, diverging type and non-branching type) from the selected area of interest in the graphical representation. The output of the classifier module 118 results in identification of a different class of rare cerebrovascular abnormalities known as cerebral venous malformations. Using the LSTM architecture allows the classifier module 118 to classify the selected area of interest into one of the many different types of cerebral venous malformations.

Figure 2:
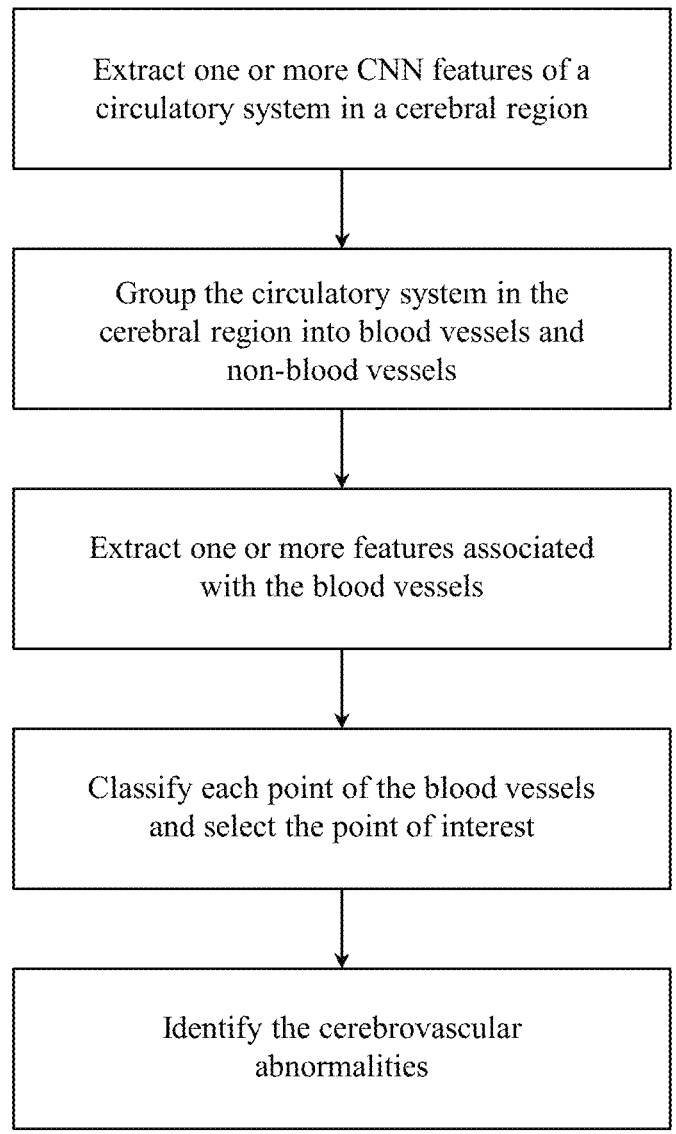
FIG. 2 illustrates a method for identifying cerebrovascular abnormalities in a subject, in accordance with various embodiments of the present disclosure.

Now referring to FIG. 2, a method for identifying cerebrovascular abnormalities in a region of interest is disclosed. In one embodiment, the method comprises the steps of receiving plurality of images from a medical imaging device such as a CT angiography by the receiver module 112 of the computing device 110. The plurality of images are pertaining to the area of interest. Specifically, the plurality of images capture the cerebral regions of the subject under diagnosis. Further, a two dimensional or three dimensional virtual representation of the circulatory system in the cerebral region is reconstructed using the plurality of images by the graphical processing module 114.

At step 205, the virtual representation of the circulatory system is provided as an input to the extraction module 116. At this step, the extraction module 116 implements a convolutional neural network architecture either on the computing device 110 or on a network of computing nodes operatively connected to the computing device 110 via a communication network. A plurality of features associated with each of the one or more spatial points in the virtual representation, referred to as CNN features are extracted. In one embodiment, a generative adversarial network (GAN) provides the training data comprising plurality of images associated with the region of interest, for extracting the CNN features.

At step 210, the virtual representation of the circulatory system is classified into blood vessels and non-blood vessels by the classifier module 118 using the extracted CNN features. As may be understood, the structure of blood vessels within the network of blood vessels in the virtual representation is of critical importance to meet the objectives of the present disclosure. Non-blood vessels captured in the virtual representation are for example tissues, collagen etc. that are filtered out by the classifier module 118 at this step.

At step 215, using the extracted CNN features or using a set of derived features, a two dimensional or three dimensional graphical representation of the network of blood vessels is generated by the graphical processing module 114. The one or more CNN features and derived features include, for example, centre of blood vessel, radius of blood vessel, texture, blood flow direction, volume of the area under consideration, relative position of the area under consideration with respect to centre of the cerebral region etc. The dimensions at the edges of the blood vessels in the blood vessel network are directly proportional to the thickness of blood vessels within the cerebral region of the subject or to the volume of blood flowing through the blood vessels.

At step 220, the classifier module 118 implements a graph convolutional network (GCN) architecture to classify each spatial position in the graphical representation of the blood vessel network into a converging type, a diverging type and a non-branching type. The graphical representation of the blood vessel network along with a plurality of extracted and derived features is provided as input to the graph convolutional network. Further, the graphical representation of the blood vessel network is annotated with the output of GCN, i.e. each spatial position in the graphical representation is colour coded or given an alphanumeric legend for example to identify the converging type, diverging type and non-branching types.

At step 225, the graphical representation is displayed on the user interface 120 for receiving a user selection of the area of interest for performing further diagnosis. The user is for example a doctor, healthcare professional. The user selection of the area of interest is received via an interactive display unit of the computing device 110, for example. Preferably, the three dimensional graphical representation of the blood vessel network is represented in an ellipsoid such that the centre of the ellipsoid corresponds with the centre of cerebral region of the subject. Further, the user selection of the area of interest is preferably received from the centre of the ellipsoid to its edges, in the form of sections, for example.

In one example, the radius of the section of interest selected by the user is correlated with the type of cerebrovascular abnormality being studied. For example, for developmental venous anomalies (DVA), typically a larger radius is selected. On the other hand, for cerebral venous malformation, multiple selections of smaller radius are selected.

At step 230, the section of interest selected by the user is provided as input to the classifier module 118. The classifier module 118 further implements a second graph convolutional network to identify attributes of rare cerebrovascular abnormalities such as DVA using the graphical representation of the selected region and the features associated with the same. In another embodiment, the one or more sections of interest selected by the user is provided as an input to a GNU-LSTM architecture implemented by the classifier module 118 to identify one or more cerebral venous malformations.

Figure 3:
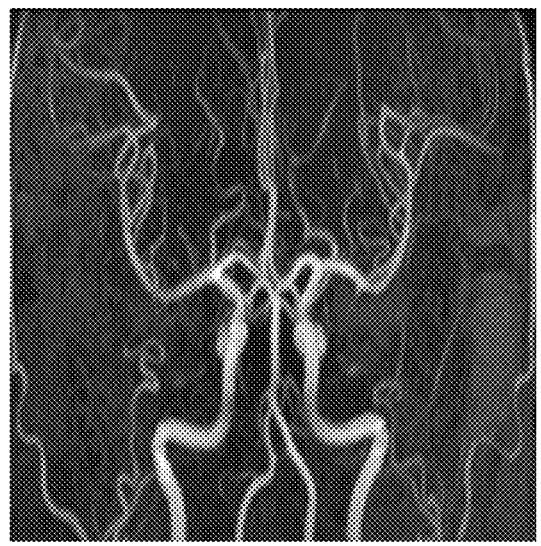
FIG. 3 illustrates images for i) a normal cerebrovascular region, ii) abnormal connection between arteries and veins leading to cerebrovascular abnormalities, and iii) arteriovenous malformations, as captured by the medical imaging device, in accordance with embodiments of the present disclosure.
Figure 3:
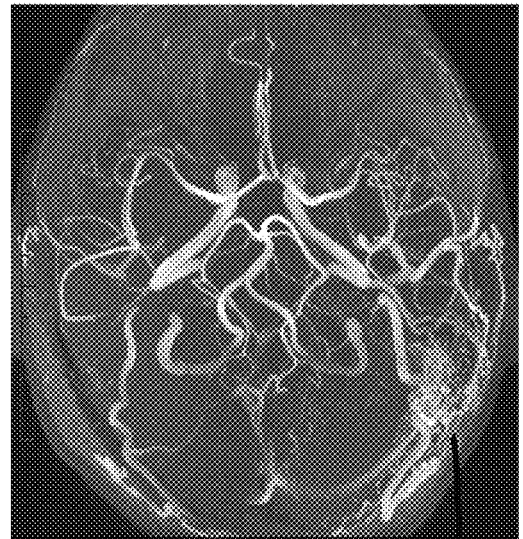
Figure 3:
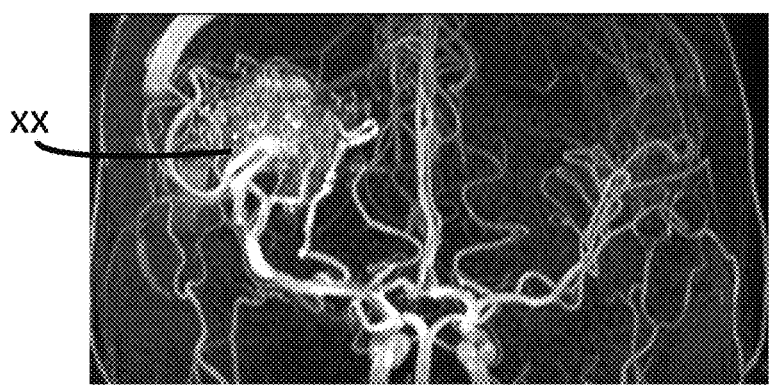

FIG. 3 shows sectional view of the cerebrovascular region of subjects captured using the medical imaging device 105 in accordance with embodiments of the present disclosure. 3A illustrates the sectional view of a normal cerebrovascular region in that no symptomatic bulges or nodes in the arteries and veins are visible. 3B illustrates a sectional view of the subject with abnormal passageway between arteries and veins at the region marked 'x'. Similarly, 3C illustrates a sectional view of the subject with arteriovenous malformations, wherein abnormal connections are formed between arteries and veins sans the capillary system.

As can be seen from FIGS. 3B and 3C, the abnormal connections between the arteries and veins generally look similar to the human eye and given that most of these cerebrovascular abnormalities have very similar symptoms, it becomes very difficult to properly diagnose a subject with a particular cerebrovascular condition. By using the system and method of present disclosure, the sectional views of the two conditions are distinguishable by way of capturing plurality of images, extracting CNN features associated with the cerebrovascular region identified in the captured images, grouping the circulatory system into blood vessels and non-blood vessels, extracting features associated with the blood vessels in the region of interest, classifying each point on the blood vessel in the region of interest and determining the cerebrovascular abnormality using embodiments of the aforementioned disclosure.

As would be evident from the foregoing disclosure, the system and method of the present disclosure are advantageous in that several types of cerebrovascular abnormalities including the rare ones that are usually not detectable using scans by medical imaging device such as CT angiography can be identified and early diagnosis can be made by virtue of the feature trained models implemented by the system of present disclosure. Further, the method allows the user to perform diagnosis for different types of cerebrovascular abnormalities with a single scan and feature trained models. Several other advantages are noticeable.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

I claim:

1. A method for identifying cerebrovascular abnormalities in a cerebral region of a subject, the method comprising:
   extracting one or more CNN features of the circulatory system in the cerebral region using a virtual representation of the cerebral region;
   grouping, based on the CNN features, the circulatory system in the cerebral region into a blood vessel type and a non-blood vessel type;
   deriving one or more additional features associated with the blood vessels;
   classifying each point of the blood vessel into one of a non-branching, diverging and converging type using a graph convolution network;
   selecting a region of interest in the virtual representation of the cerebral region, wherein the region of interest comprises the one or more points of the blood vessel; and
   identifying the cerebrovascular abnormalities using the extracted one or more features associated with the blood vessel or the classification of the blood vessel or both at the region of interest.

2. The method as claimed in claim 1, wherein the cerebrovascular abnormalities identified include one of developmental venous anomaly or cerebral venous malformations.

3. The method as claimed in claim 1, wherein the virtual representation of the cerebral region of a subject is one of a two dimensional or a three dimensional representation.

4. The method as claimed in claim 1, wherein the virtual representation of the cerebral region comprising the circulatory system is generated using a plurality of images captured by a medical imaging device.

5. The method as claimed in claim 1, wherein the one or more derived features of the blood vessels comprises centre of the blood vessels, radius of the blood vessels, texture of the blood vessels, blood flow direction, volume of the blood vessels, and relative position of the blood vessels with respect to the centre of the cerebral region.

6. The method as claimed in claim 1, wherein classifying each point of the blood vessel into a non-branching, diverging and converging type comprises the steps of reconstructing the blood vessel using the extracted features and wherein the edges of the blood vessel are directly proportional to one of blood vessel thickness or volume of blood vessel.

7. The method as claimed in claim 1, wherein identifying the cerebrovascular abnormalities comprises identifying aneurysm.

8. A system for identifying cerebrovascular abnormalities in a cerebral region of a subject, the system comprising:
   a medical imaging device configured for capturing one or more images of the cerebral region of the subject;
   a computing device configured for executing the steps for identifying the cerebrovascular abnormalities, the computing device comprising:
   a receiving module configured for receiving the one or more images from the medical imaging device;
   a graphical processing module configured for generating a virtual representation of the cerebral region;
   an extractor module configured for implementing one or more variants of the convolutional neural network and extracting one or more high resolution output features associated with one or more blood vessels in the virtual representation of the cerebral region generated using the graphical processing module;
   a classifier module configured for classifying the blood vessel into one of a non-branching type, converging type and diverging type, and
   a graphical display configured for displaying a virtual representation of the cerebral region comprising one or more blood vessels, wherein the computing device is configured for receiving a selection of a region of interest in the virtual representation for identifying one or more cerebrovascular abnormalities.

9. The system as claimed in claim 8, wherein the extractor module is configured for communicating with a network of computers for extracting CNN features associated with the circulatory system of the cerebral region.

10. The system as claimed in claim 8, wherein the system is configured for identifying the cerebrovascular abnormalities related to aneurysm.

* * * * *